United States Patent [19]
Greco

[11] Patent Number: 5,312,385
[45] Date of Patent: May 17, 1994

[54] DEVICE FOR PROTECTED PULSE IRRIGATION

[75] Inventor: Richard J. Greco, Pittsburgh, Pa.

[73] Assignee: University of Pittsburgh, Pittsburgh, Pa.

[21] Appl. No.: 775,301

[22] Filed: Oct. 9, 1991

[51] Int. Cl.$^5$ .............................................. A61B 19/00
[52] U.S. Cl. ................... 604/356; 604/289; 604/293; 604/408; 128/DIG. 24; 602/3
[58] Field of Search ................... 128/849-855, 128/DIG. 24; 604/289, 290, 293, 294, 319, 356, 408, 412; 606/131; 602/3

[56] References Cited

U.S. PATENT DOCUMENTS

| | | | |
|---|---|---|---|
| 3,186,404 | 6/1965 | Gardner | 602/3 |
| 3,288,140 | 11/1966 | McCarthy | 604/289 |
| 3,713,423 | 1/1973 | Sparr, Sr. | 604/289 |
| 3,744,491 | 7/1973 | Fischer | 604/293 |
| 4,161,179 | 7/1979 | Abramson | 128/DIG. 24 |
| 4,772,259 | 9/1988 | Frech et al. | 604/293 |
| 4,790,815 | 12/1988 | Balteau et al. | 604/408 |
| 4,991,593 | 2/1991 | Le Vahn | 128/DIG. 24 |

FOREIGN PATENT DOCUMENTS 0114443 12/1941 Australia .............................. 604/290

Primary Examiner—Paul Prebilic
Attorney, Agent, or Firm—Reed Smith Shaw & McClay

[57] ABSTRACT

The present invention provides an apparatus and method for performing protected pulse irrigation. An impervious collapsible enclosure is provided to encompass that portion of the body upon which the area to undergo pulse irrigation is located. The enclosure provides the person performing pulse irrigation with the freedom of movement and visibility necessary to adequately irrigate the area of interest, while preventing contact with contaminated irrigation fluid and other biological materials.

1 Claim, 3 Drawing Sheets

DEVICE FOR PROTECTED PULSE IRRIGATION

FIELD OF THE INVENTION

The present invention relates to a method and device for preventing the spread of infectious bacteria and viruses, and more particularly, to an impervious enclosure and method of using such enclosure during pressure or pulse irrigation to isolate those in proximity to the patient from splashed, aerosolized or otherwise escaping irrigation materials.

BACKGROUND OF THE INVENTION

Pressure or pulse irrigation has been shown to decrease infection rates in open wounds. During pulse irrigation the wound is bathed with a small stream of compressed air/fluid (generally a saline solution) at relatively high pressure to dislodge dead tissue and foreign contamination. Pressures up to 70 to 75 psi are used to attain the desired beneficial results. As little as 250 cc of irrigation fluid may be used in the procedure, but often as much as three (3) to six (6) liters of fluid are used to ensure proper cleansing and of the wound and removal of end coverage. Many hand, foot and other open injuries occur each year for which pulse irrigation provides beneficial results. Additionally, pulse irrigation is used in a number of operative procedures such as prosthetic joint replacement, in which it is used to remove bone fragments from the area of prosthesis.

Under current practices, however, the person performing the pulse irrigation and those other surgical support personnel in the immediate area are placed at risk of contracting infectious diseases borne in contaminated irrigation materials which splash off the open wound (including an area of surgery), are aerosolized or otherwise escape into the surrounding atmosphere. Some pulse irrigation systems are equipped with partial shields to prevent splashing of contaminated materials directly back toward the operator, but do not prevent peripheral splashing (which can soak the shoes of the operator and others in the periphery as well the floor and drapes) or aerosolization. The resultant risk of infection from such escaping materials during treatment of wounds in individuals with infectious diseases, such as AIDS and hepatitis, makes pulse irrigation a possibly dangerous procedure to a treating physician and attending staff. It would therefore be highly desirable and advantageous to develop an enclosure system for use during pulse irrigation to isolate contaminated irrigation fluids and tissue from those persons in proximity to the patient.

Even before the recent discovery of the benefits of pulse irrigation, wounds have been treated with numerous fluids using a number of procedures to induce proper healing. Various enclosures have been developed to keep such fluids in proximity to the wound undergoing treatment. In U.S. Pat. No. 3,288,140 issued to McCarthy, for example, a method and apparatus for treatment of surface wounds by fluids is disclosed. The McCarthy apparatus comprises a cup or chamber into which a fluid is introduced. The cup provides a sealed chamber around the wound. The cup is first filled with fluid and then additional fluid is injected through an inlet to create a stirred bath. The apparatus is also provided with an outlet located above both the wound and the inlet to allow excess fluid to exit the cup or chamber. The cup is manufactured from plastic, hard rubber, porcelain and other materials impervious to the fluid being used. The inlet tube is disposed within the cup so as to allow angular movement but to prevent axial movement. The patient being treated with the device can thus change the angle of the inlet tube to direct the path of incoming fluid to different areas of the wound.

The use of fluids in treating infections has also been used in the treatment of animals. In U.S. Pat. No. 2,839,052, issued to Verch, et al., a device for treating infections in animals is disclosed. The device is particularly suited to the treatment of mastitis infection in female animals, and is particularly directed to the infection of the mammary glands of cows. The Verch, et al. device includes a cup or chamber into which an inlet tube is connected. Fluid is introduced into the chamber so as to create a turbulent flow around the affected area similar to the action of a whirlpool. The stimulation of the affected area causes an increase in blood flow to that area, which helps in the treatment of the infection.

A similar device for the washing and cleansing of an udder and teat is disclosed in U.S. Pat. No. 3,713,423 issued to Sparr. The Sparr device includes a cup which is positioned to accommodate the teat of a COW. The bottom of the cup includes a valving means having an enclosed nipple which aims the solution towards the opening of the teat where the infection (mastitis) usually starts. The solution in the cup is in a state of swish-swashing turbulence and is suitably drained via an outlet tube.

Cups or chambers into which an irrigating fluid is injected have also been used to remove obstructions from the human eye. In U.S. Pat. No. 4,798,599, issued to Thomas, for example, an eye cup having a rim portion that conforms to the orbit portion which surrounds the eye is disclosed. The eye cup is placed over the eye and forms a liquid-confining chamber adjacent to the eye. The skin above and below the eye is drawn away from the eye with the eye cup being pushed against the skin so that the rim portion applies sufficient pressure against the skin to hold the eye open. Eyewash is delivered to the eye and drained from the chamber via inlets and outlets, respectively. The eyewash is delivered into the chamber so as to contact the side of the eye and not the cornea directly, thereby preventing blepharal spasms.

Portable enclosures or chambers have also been used in connection with the inducement of healing of wounds by hyperbaric oxygenation treatment. In U.S. Pat. No. 4,772,259, issued to Frech, et al., a hyperbaric oxygenation apparatus comprising a chamber in the form of a disposable inflatable bag of impervious, synthetic resinous material is disclosed. The chamber is designed to fit over the affected area and forms a non-leak enclosure into which oxygen can be introduced through a single port in fluid connection with the chamber. The pressure of the oxygen in the chamber is pulsated between maximum and minimum positive values. The patient cyclically experiences first a medicinal increase in the blood gas level in the limb under treatment with a corresponding restrictive blood flow and, thereafter, a progressive return to normal blood flow rates in the limb of the patient as the pressure in the chamber changes from maximum to minimum positive pressure. The pressure loss problem associated with prior portable hyperbaric oxygenation apparatus was solved by a novel cuff or sleeve preventing inversion under positive pressure. A portable hyperbaric oxygen chamber is also disclosed in U.S. Pat. No. 3,744,491.

Similarly, in U.S. Pat. No. 3,610,238, issued to Rich, a wound infection prevention device is disclosed which comprises a porous pad encased in an air-impervious bag to which the upper and lower surfaces of the pad are attached. The device includes an annular channel surrounding the periphery of the pad to which air may be fed under pressure via a single air inlet port. The device is placed around a wound on the skin of the patient and air is fed into the annular chamber. The air passes through the porous pad and then flushes upwardly over the wound to prevent dust and airborne bacteria from falling upon the wound.

None of the above devices provides a chamber or enclosure suitable for use during pulse irrigation of a wound to isolate contaminated materials from those persons in the immediate area of the procedure. Enclosures previously designed for use with liquid treatment cannot withstand the relatively high pressures used in pulse irrigation without leakage, aerosolization or other escapage of the liquid or contaminated material. The person performing pulse irrigation also needs to have an unobstructed view of the wound. Furthermore, the operator should have freedom to maintain substantially complete control over the position of the pulse irrigation nozzle to adequately control the direction of the pulse. Moreover, because pulse irrigation is used under the time constraints experienced in operating room and emergency room procedures, a device developed for use with pulse irrigation should be capable of quick yet substantially fail-safe application.

SUMMARY OF THE INVENTION

Accordingly, the present enclosure system and method allow for isolation of those in the vicinity of the pulse irrigation patient from contaminated pulse irrigation materials such as spent irrigation fluid and any dislodged biological matter. Generally, the present enclosure system comprises a collapsible enclosure formed of an impervious material of appropriate size to enclose the body portion upon which the wound is located, at least one port for insertion of a pulse irrigation nozzle, and at least one outlet port to allow drainage of contaminated irrigation materials. The present enclosure system is inexpensive and can be made operational in very little time. Use of an enclosure manufactured from a transparent, synthetic polymer allows unobstructed observation of the wound during pulse irrigation. Furthermore, the collapsible nature of the enclosure allows ease of movement of the irrigation pulse nozzle in three dimensions to ensure proper irrigation of the wound.

DESCRIPTION OF THE PREFERRED EMBODIMENTS

The risk of transmitting bacteria and viruses, such as the H.I.V. and hepatitis viruses, to health care workers during pulse irrigation defines an urgent need to develop an enclosure system to contain contaminated pulse irrigation materials during such a procedure.

Figure 1:
FIG. 1 is a side view of a first embodiment of the present enclosure system having a single open end for insertion of a wounded body part.

With reference to FIG. 1, such an enclosure system 1 is illustrated comprising an elongated, collapsible enclosure 2 formed of an impervious material or materials of appropriate size to encompass the body part (e.g., the arm, leg or head or any part thereof) upon which a wound W to be treated is located. The material of which collapsible enclosure 2 is manufactured should be of sufficient strength to withstand the stress imposed by the pressure of pulse irrigation without fluid leakage aerosolization or other escapage of fluid or contaminated materials. Pressures of 70 to 100 psi are commonly used.

The material is also preferably transparent to enable the operator to adequately view wound W during pulse irrigation. The entirety of enclosure 2 may be transparent, or alternatively, only that portion of enclosure 2 in the vicinity of the wound may be transparent. Enclosure system 1 should also preferably allow free movement of the pulse irrigation nozzle in three dimensions to enable complete treatment of wound W. The collapsible nature of the construction material or materials allows such freedom. The material should also preferably be capable of sterilization using common sterilization procedures. A number of synthetic polymers commercially available are suitable for this purpose. Suitable materials from which the enclosure may be manufactured include polyethylene or polypropylene, or copolymers thereof. The preferred polymer from which the enclosure may be manufactured -is polyethylene.

To ensure that no contaminated irrigation fluids come in contact with the operating room staff, it is necessary to supply any enclosure according to the present invention with a means of forming a substantially water-tight seal at each open end of such enclosure. Enclosure 2, as illustrated in FIG. 1, has only one open end. Because the entire body is not enclosed, at least one end of any enclosure according to the present invention will be sealed in juxtaposition to the patient's skin. In some cases both ends may be sealed in such a manner.

The nature of synthetic polymers suitable for the present use allows formation of a substantially water-tight or non-leaking seal upon human skin under application of moderate occlusive pressure. Several different means of providing a substantially non-leaking seal can thus be used. Referring to FIG. 1, end sealing means 3 can be a drawstring or VELCRO ® strap. Moreover, adhesive tape, elastomeric bands or other external devices causing occlusion of the material around the patient's skin can be used. The means for providing a substantially non-leaking seal can also be an inflatable bladder which is inflated to conform snuggly to the area of the patients body upon which the seal is to be formed. The inflatable bladder may be an integral part of collapsible enclosure 2 or may be separably placed around the appropriate area of collapsible enclosure 2 to provide occlusive pressure.

Collapsible enclosure 2 also comprises at least one means 4 to allow insertion of a disposable or reusable pulse irrigation nozzle 5. Inlet means 4 can be a self-sealing diaphragm into which pulse irrigation nozzle 5 is inserted. Alternatively, enclosure 2 may be manufactured with pulse irrigation nozzle 5 as an integral part of enclosure 2. To enable easier access to wounds located throughout the body, more than one inlet means 4 can be disposed at various positions upon enclosure 2.

Enclosure 2 is also supplied with at least one exit port 6 to allow drainage of contaminated irrigation materials. Preferably exit port 6 is shaped in the form of a funnel and placed at the lowest point of enclosure 2 as shown in FIG. 1 to maximize collection of irrigation materials. Upon collection at exit port 6, the contaminated irrigation materials are preferably drained through a plastic tube 7 of adequate diameter to allow the contaminated materials to egress as fast as the inflow of fresh irrigation fluid. Multiple exit ports may be used. The spent irrigation fluid can be drained into a separate container (not shown) for proper disposal.

Figure 2:
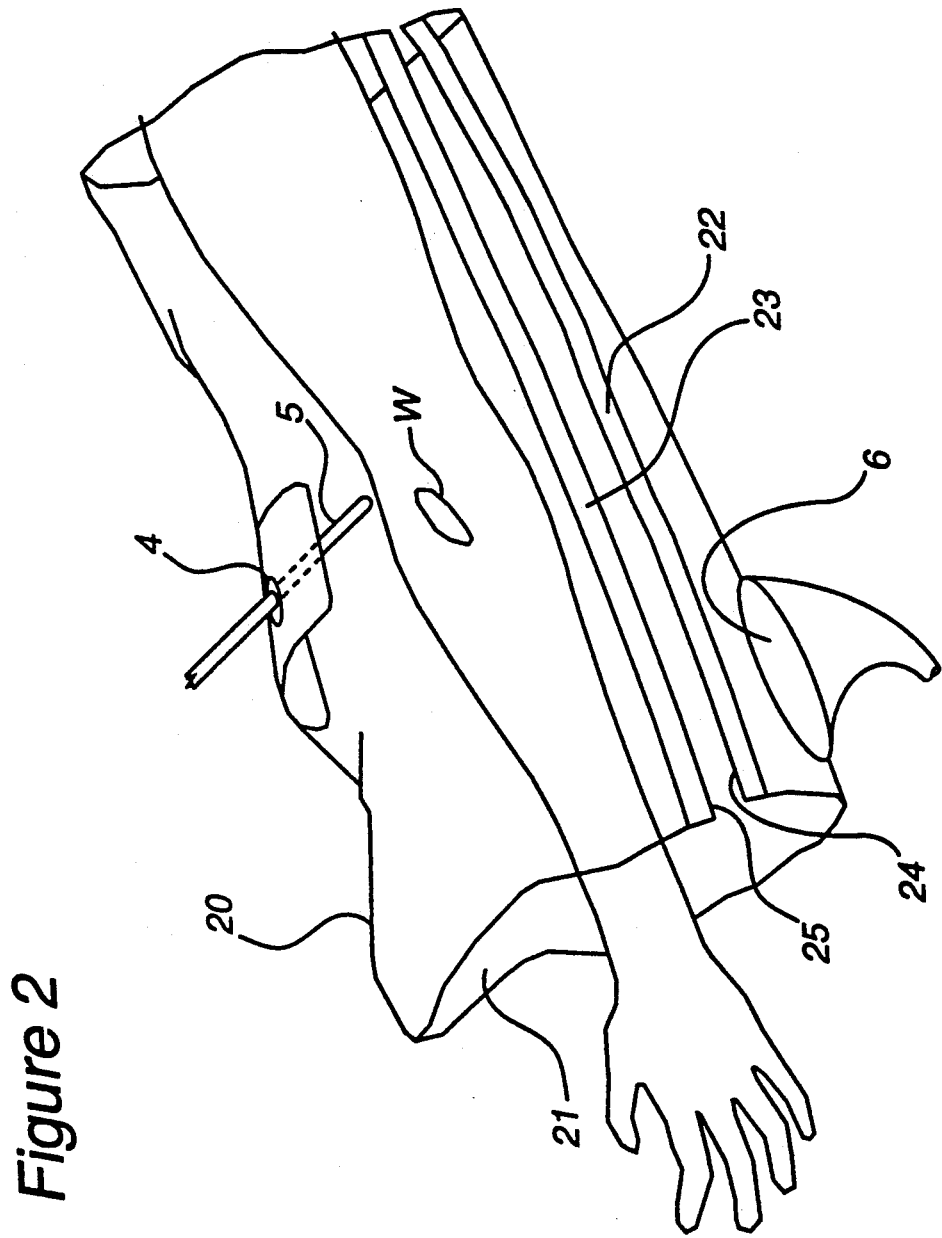
FIG. 2 is a side view of a second embodiment of the present enclosure system in which a sheet of appropriate synthetic material is wrapped around the wounded body part and sealed to form a non-leaking enclosure.

Referring to FIG. 1, at least one distal end 8 of collapsible enclosure 2 must initially be open to allow the body part upon which wound W is located to be inserted within enclosure 2. In some applications it may be preferable to use enclosures in which both ends are initially open. In other applications, it may be preferable to provide a sheet of synthetic material 20 as shown in FIG. 2 which can be wrapped around the body part of interest in a cylindrical fashion and connected to form a seam (not shown) along the axial length of resultant open-ended cylinder 21. Any number of means of forming a water-tight seam capable of withstanding pressures associated with pulse irrigation can be employed. Adhesive strips 22 and 23 can be placed at each lateral end 24 and 25 of the synthetic sheet 20 and adhered to form such a seam. Alternatively, male/female plastic couplings similar to those used in ZIP-LOC ® bags can be utilized to form a substantially non-leaking seam. An external clamping means can also be used. Cylinder 21, as illustrated in FIG. 2, would require two end sealing means (not shown) to complete a closed, non-leaking enclosure. Again, such end sealing means can include VELCRO ® strapping, draw strings, elastomeric bands, inflatible bladders or other suitable closure techniques and materials.

Figure 3:
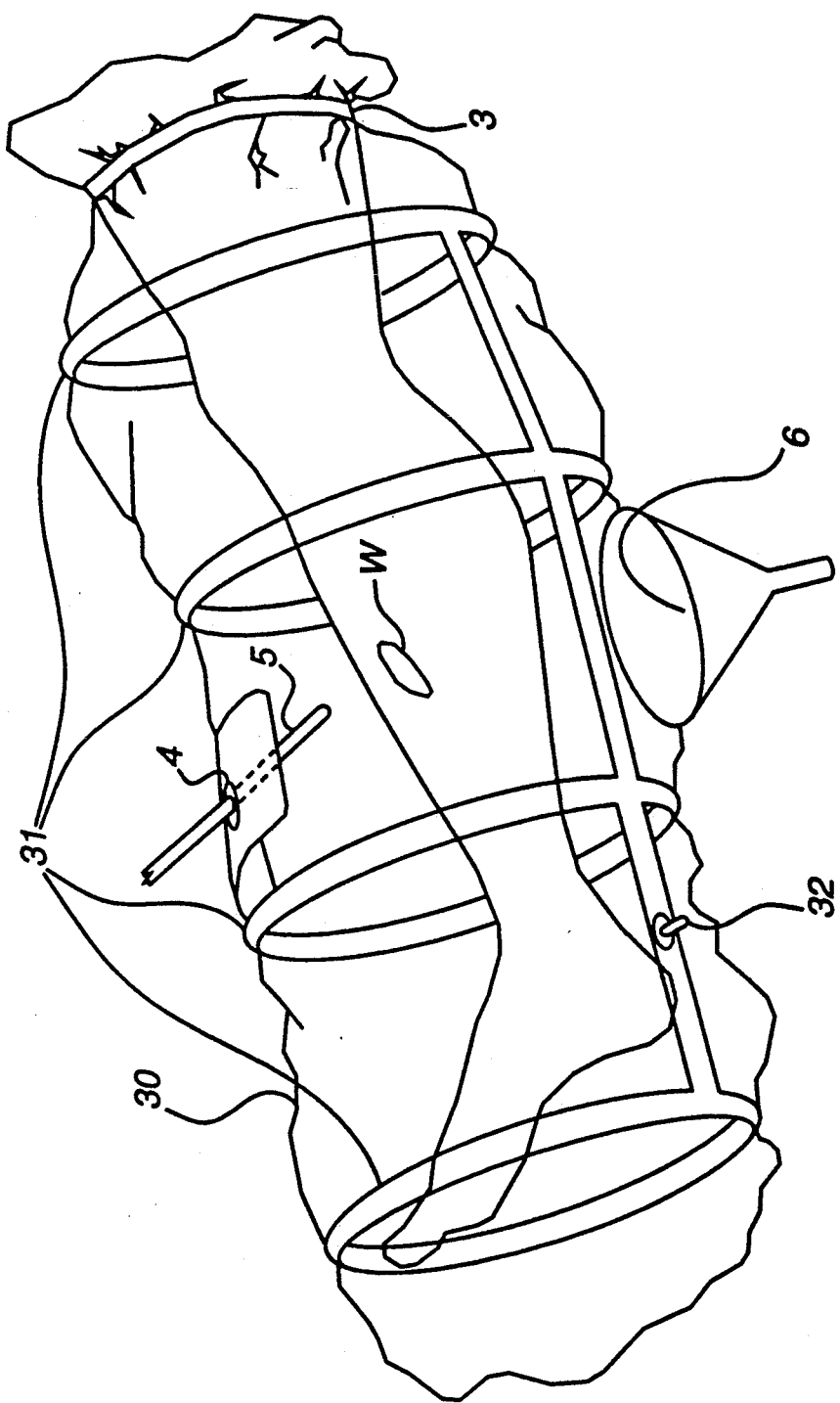
FIG. 3 is a side view of a third embodiment of the present enclosure system having support means to support the enclosure away from the wounded body part.

With reference to FIG. 3, to enable unobstructed access to wound W being treated, enclosure 30 may include support means 31 to maintain enclosure 30 in a position away from the body part being treated. As shown in FIG. 3, a preferred manner of providing such support means 31 is to dispose inflatable ribbing disposed upon enclosure 30 which can be inflated via valve 32 to keep enclosure 30 away from the body part. Alternatively, each rib may be provided with its own valve. Inflatable ribbing 31 may be inflated to varying degrees to provide the desired amount of support. Alternatively, plastic or metal ribbing can be disposed at various positions upon enclosure 30 to provide the desired support.

Although the invention has been described with reference to certain embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that the appended claims will cover such modifications that fall within the true scope of the invention.

What is claimed is:

1. An enclosure system for use during pulse irrigation of a wound on a body part of a patient to isolate contaminated irrigation materials from persons in proximity to the patient, comprising:
   a. a collapsible enclosure of sufficient size to encompass the body part upon which the wound is located, said enclosure having at least one opening for insertion of the body part, said enclosure further being constructed of an impervious material of sufficient strength to withstand pressures used during pulse irrigation;
   b. at least one means disposed upon said enclosure for inserting a pulse irrigation nozzle in a substantially non-leaking manner;
   c. at least one outlet port to allow drainage of contaminated irrigation materials; and
   d. a support means for supporting said enclosure away from the patient's body port, said support means comprising inflatable ribbing disposed upon said enclosure.

* * * * *